(12) United States Patent
Heigl et al.

(10) Patent No.: US 7,568,837 B2
(45) Date of Patent: Aug. 4, 2009

(54) METHOD FOR ACTIVATING AN X-RAY IMAGE RECORDING SYSTEM AND AN X-RAY IMAGE RECORDING SYSTEM

(75) Inventors: Benno Heigl, Coburg (DE); Norbert Rahn, Forchheim (DE); James Williams, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/077,685

(22) Filed: Mar. 20, 2008

(65) Prior Publication Data
US 2008/0232554 A1 Sep. 25, 2008

(30) Foreign Application Priority Data
Mar. 20, 2007 (DE) ................... 10 2007 013 322

(51) Int. Cl.
*A61B 6/02* (2006.01)
(52) U.S. Cl. ...................................................... 378/207
(58) Field of Classification Search ................ 378/4, 378/207
See application file for complete search history.

(56) References Cited

U.S. PATENT DOCUMENTS

| | | | | | |
|---|---|---|---|---|---|
| 4,296,329 | A | * | 10/1981 | Mirabella | 378/20 |
| 6,044,132 | A | * | 3/2000 | Navab | 378/207 |
| 6,678,353 | B2 | * | 1/2004 | Graumann et al. | 378/207 |
| 6,869,217 | B2 | | 3/2005 | Rasche et al. | |
| 7,010,095 | B2 | * | 3/2006 | Mitschke et al. | 378/207 |
| 2001/0005410 | A1 | | 6/2001 | Rasche et al. | |
| 2002/0080909 | A1 | * | 6/2002 | Op De Beek et al. | 378/207 |
| 2004/0114709 | A1 | * | 6/2004 | Griffith | 378/4 |
| 2005/0047552 | A1 | * | 3/2005 | Arai et al. | 378/207 |
| 2008/0240363 | A1 | | 10/2008 | Grebner et al. | |

FOREIGN PATENT DOCUMENTS

DE 19958864 A1 6/2001
DE 10 2005 012 700 A1 9/2006

OTHER PUBLICATIONS

Karl Wiesent et al.; Enhanced 3D-Reconstruction Algorithm for C-Arm Systems Suitable for Interventional Procedures; IEEE Transactions on Medical Imaging, vol. 19, No. 5, May 2000; Magazine; 2000; US.
"Technical Factors of CT Angiography Studied with a Cartid Artery Phantom", AJNR Am J Neuroradiol 18:401-408, Mar. 1997, by S.W. Wise, K. D. Hopper, T. A. Schwartz, T. R. Ten Have, C. J. Kasales; Magazine; 1997; US.
"Stair-Step Artifacts with Single versus Multiple Detector-Row Helical CT", Radiology 2000, 216: 185-196, by D. Fleischmann, G.D. Rubin, D. S. Paik, S. Y. Yen, P. R. Hilfiker, C. F. Beaulieu, S. Napel; Magazine; 2000; US.

* cited by examiner

*Primary Examiner*—Chih-Cheng G Kao

(57) ABSTRACT

To make optimum use of an x-ray image recording system with an x-ray C-arm, which has an x-ray radiation source and an x-ray detector and can be pivoted about any axis, 2D axis lines are plotted in two x-ray images of an object to be imaged more precisely and these 2D axis lines are used to define a 3D axis line and the x-ray image recording system is set so that it can be directly pivoted precisely about this 3D axis line. A sequence of x-ray images is then recorded in positions of the x-ray C-arm, between which the same can be pivoted about this defined axis. This displays the object optimally.

16 Claims, 1 Drawing Sheet

METHOD FOR ACTIVATING AN X-RAY IMAGE RECORDING SYSTEM AND AN X-RAY IMAGE RECORDING SYSTEM

CROSS REFERENCE TO RELATED APPLICATIONS

This application claims priority of German application No. 10 2007 013 322.9 filed Mar. 20, 2007, which is incorporated by reference herein in its entirety.

FIELD OF THE INVENTION

The invention relates to a method for activating an x-ray image recording system with an x-ray C-arm, which has an x-ray radiation source and an x-ray detector and can be pivoted about any axis. The invention also relates to an x-ray image recording system, comprising an x-ray C-arm with an x-ray radiation source and an x-ray detector, it being possible to pivot the x-ray C-arm about any axis.

BACKGROUND OF THE INVENTION

With conventional x-ray C-arm systems it is not possible to pivot the x-ray C-arm about any axis.

DE 10 2005 012 700 A1 discloses an x-ray image recording system, wherein the support (x-ray C-arm) is attached to the hand of a robot having six axes of rotation. As a result the support can be moved into any position and can be pivoted about any axis. It is by no means simple to operate such an x-ray image recording system, so the possibilities offered by said x-ray image recording system are not necessarily utilized optimally. The infinite settings for the x-ray C-arm as support essentially allow customized imaging of quite specific objects, whose main axis does not correspond to the axis of the body of the patient. It is possible to record image sequences, in which the support is pivoted about this main axis of the object. To this end this main axis of the object must however be known at least once and then the x-ray image recording system must be activated so that it actually rotates about this main axis.

SUMMARY OF THE INVENTION

The object of the present invention is to support and thereby to simplify the utilization of the extended possibilities offered by an x-ray image recording system, whose support can be pivoted about any axis.

The object is achieved by a method and an x-ray image recording system with the features of the claims.

The inventive method therefore comprises the steps:
a) Activating the x-ray image recording system (for example after receipt of an input by an operator) such that the x-ray C-arm takes up a first position and bringing about the recording of a 2D x-ray image in the first position as a first 2D x-ray image,
b) Activating the x-ray image recording system (for example after receipt of a further input by an operator) such that the x-ray C-arm takes up a second position and bringing about the recording of a 2D x-ray image in the second position as a second 2D x-ray image,
c) Establishing the profile of a 2D axis line in relation to an identifiable object in the 2x-ray images in the coordinates of the first 2D x-ray image,
d) Establishing the profile of a 2D axis line in relation to the object in the coordinates of the second 2D x-ray image,
e) Back-projecting the profiles of the two 2D axis lines into a volume element space and determining the profile of a 3D axis line in the volume element space from the two back-projected 2D axis lines (which either correspond or with which two 3D axis lines are formed by the back-projection and the 3D axis line determined by averaging runs between these 3D axis lines),
f) Automatically activating the x-ray image recording system (without axis definition by user input) such that the x-ray C-arm takes up a number of positions one after the other, which follow from each other by pivoting the x-ray C-arm about the 3D axis line, and bringing about the recording of a 2D x-ray image in at least two of the positions.

According to the invention therefore two images of an object are used to establish an object axis, about which the x-ray C-arm is to rotate during subsequent image recordings.

In a first embodiment the 2D axis lines are established by an operator, in other words steps c) and d) respectively comprise the receipt of an input of at least two coordinate points by such an operator, for example with the aid of a computer mouse, with the two coordinate points defining the 2D axis lines, in that they are generally connected to each other. With this embodiment of the invention use is made of the fact that an operator can recognize the object in the x-ray images particularly reliably, in particular distinguishing it from other imaged objects. It is thus possible to utilize the experience of a physician for example.

So that the inputs in relation to the first and second x-ray images are not contradictory, in a preferred embodiment provision is made after step c) for each of the input coordinate points of the first 2D x-ray image to be back-projected into a volume element space as a 3D line. The two 3D lines are then forward-projected into the coordinate system of the second 2D x-ray image and displayed to the operator in the second 2D x-ray image (before said operator makes the input for receipt in step d)). The two coordinate points established by the operator in the second 2D x-ray image must lie on the two lines. The back-projections of the two 2D axis lines then correspond in one 3D line, i.e. the 3D axis line is defined uniquely. This avoids the 3D axis line having to be determined by calculating the profile of a center line between two different 3D axis lines.

In addition to the definition of the object axis as the pivot axis for the x-ray C-arm, with a longitudinally extended object it is of course also relevant which part of the object is to be displayed where in the x-ray image. The center point of the object should preferably be displayed at the center point of the x-ray image. The so-called isopoint of the x-ray C-arm is used to achieve this. This is a marked point, defined between the x-ray radiation source and detector of the x-ray C-arm. When establishing the profile of at least one of the 2D axis lines, preferably both, it is then possible to define a point on the axis of the 3D axis, which should come to lie where the isopoint of the x-ray C-arm lies. The method therefore preferably comprises the receipt of inputs to establish a 2D coordinate point on the 2D axis lines in relation to each 2D x-ray image or this 2D coordinate point is established by calculation based respectively on the inputs of two coordinate points in relation to the first and/or second 2D x-ray image (for example as the center point between the two coordinate points on the 2D axis line defined by the two coordinate points). The method then also comprises the definition of a marked 3D coordinate point on the 3D axis line from the two 2D coordinate points on each axis line in the back-projection (using conventional methods, possibly with the aid of an averaging operation) and in step f) the x-ray image recording is activated in such a manner that it is set so that the marked point defined in relation to the x-ray C-arm (isopoint) corresponds to the 3D coordinate point on the 3D axis line. Then in the image sequence recorded as part of step f) the center of the object is actually imaged in the center of the x-ray images, by pivoting about the 3D axis line from different perspectives.

Until now the embodiment was used, in which points are established by an operator. However the method can also implement establishing steps c) and d) automatically: steps c) and d) can also comprise an image recognition method, which recognizes the structure of the object (based on a predefined sample structure) and establishes a marked axis line in relation to this structure (for example based on an axis of the sample structure or using other methods, in which weightings of the gray-scale values play a part for example).

It is also possible here of course, to establish the 3D axis line uniquely, in other words to avoid contradictions, to take the result of step c), in other words the determined 2D axis line, into account in step d). After step c) then two coordinate points of the 2D axis line of the first 2D x-ray image are back-projected into a volume element space as a 3D line and the two 3D lines are forward-projected into the coordinate system of the second 2D x-ray image and then used as support in the image recognition method in step d) (specifically so that the points for defining the new axis line must lie on the two forward-projected lines).

Even with the automatic method it is again ultimately possible to achieve an optimum setting in relation to the isopoint. If therefore a marked point is defined between the x-ray radiation source and x-ray detector of the x-ray C-arm, the image recognition method can determine a marked 2D coordinate point on the 2D axis lines in the first and/or second 2D x-ray image in steps c) and d) respectively (for example based on a comparison with a predefined sample structure, for which a center point is defined), then in step e) a 3D coordinate point on the 3D axis line should be derived from these two 2D coordinate points and finally the x-ray image recording system should be activated in such a manner in step f) that it is set so that the marked point defined in relation to the x-ray C-arm corresponds to the 3D coordinate point on the 3D axis line.

With some of the objects the position and orientation in space can be determined with the aid of a sensor system. A so-called 5D or 6D position/orientation sensor is then referred to, with which three coordinates are determined for position and two or three data items are output relating to orientation. One example of such a sensor is the NaviStar catheter by Biosense Webster. The use of such a sensor is particularly expedient, if the object to be imaged by the x-ray image sequence in step f) is not part of the patient's body but is introduced into the patient's body itself. The sensor then simply has to be secured to the introduced object. An example of such an introduced object is any catheter or even a stent.

The coordinate system of the sensor is not necessarily identical to the coordinate system of the x-ray image recording system, so that an assignment has to take place before the sensor data can be used. This assignment takes place based on the imaging of the sensor in the first and second 2D x-ray images. If a sensor introduced into the object in the patient or a sensor secured to the object can be recognized in the first and second x-ray image, emitting three position data items and at least two orientation data items, the coordinate system of the sensor is assigned correctly in respect of position and dimension to the coordinate system of the x-ray image recording system based on the first and second 2D x-ray image (this is a description of what is known as registration). The data emitted by the sensor is then used to establish the 2D axis lines, because the correct position and dimension assignment allows the position and/or orientation data emitted by the sensor to be transformed into the coordinate system of the x-ray images, because the registration process has determined a set of imaging rules between the coordinate system. Steps e) and f) of this embodiment of the method can then be implemented as with the other embodiments based on the established 2D axis lines.

The invention also comprises an x-ray image recording system, comprising an x-ray C-arm with an x-ray radiation source and an x-ray detector, it being possible to pivot the x-ray C-arm about any axis. The x-ray image recording system should be designed, for example when suitably programmed in an associated microprocessor, to calculate a 3D axis line from two 2D axis lines established in relation to x-ray images recorded in different positions of the x-ray C-arm and to take up a position (in particular automatically) in such a manner that the 3D axis line corresponds to an axis about which the x-ray C-arm is then pivoted to record an x-ray image sequence.

The x-ray image recording system can be designed to receive inputs to establish a 2D axis line in relation to an x-ray image, for example by connecting a computer mouse. Alternatively the x-ray image recording system can be designed to carry out image recognition of an object displayed in an x-ray image and to define a 2D axis line in relation to the object.

The x-ray image recording system is preferably an x-ray image recording system of the type mentioned in the introduction, wherein the x-ray C-arm (support) is attached to the hand of a robot having six axes of rotation.

The object of the invention is also achieved by a method, wherein two x-ray images do not necessarily have to be recorded beforehand. This method comprises the steps:

k) Supplying a sensor that can be introduced into the body of a patient and which emits three position data items and at least two orientation data items in a coordinate system, the position of which is fixed and known in relation to the coordinate system of the image recording system, l) Receiving the three position data items and the at least two orientation data items with the sensor introduced into the body of a patient in the x-ray image recording system, m) Deriving a 3D axis line defined in a volume element space from the position and orientation data items received in step l), n) Automatically activating the x-ray image recording system in such a manner that the x-ray C-arm takes up a number of positions one after the other, following from each other by pivoting the x-ray C-arm about the 3D axis line, and bringing about the recording of a 2D x-ray image in at least two of the positions.

With this aspect of the invention the step of registering can be dispensed with by calibrating the sensor to the x-ray image recording system, in other words the data emitted by the sensor can be directly related to the coordinates of different x-ray images based on a known relationship between the coordinate systems of the sensor and the x-ray image recording system. The absence of any need for registration means that the two 2D x-ray images no longer have to be recorded beforehand.

BRIEF DESCRIPTION OF THE DRAWINGS

A preferred embodiment of the invention is described below with reference to the drawing, in which.

DETAILED DESCRIPTION OF THE INVENTION

Figure 1:
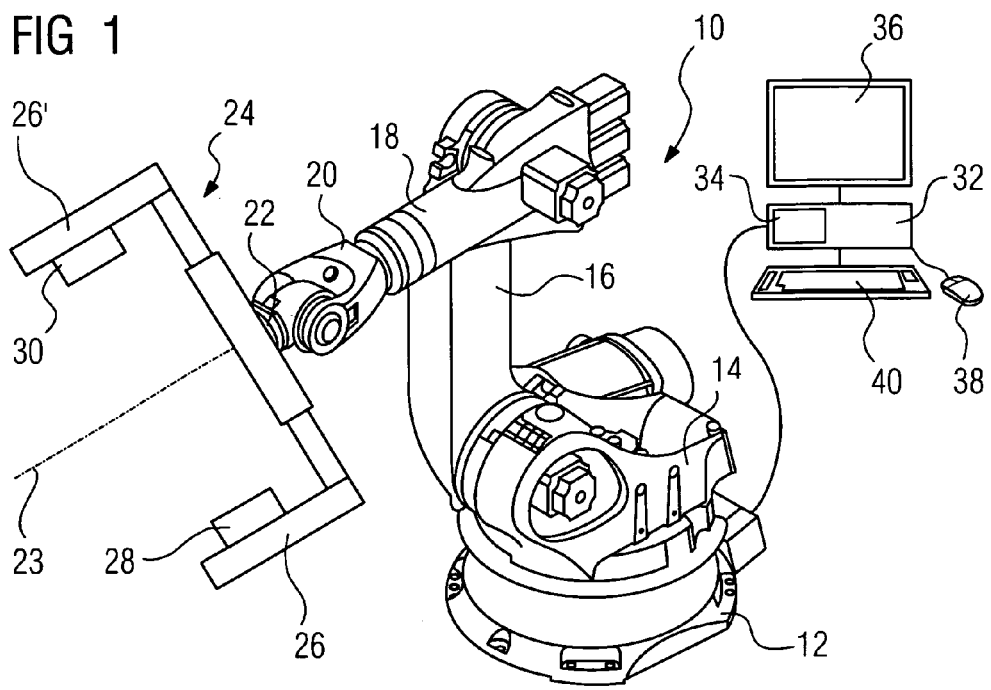
FIG. 1 shows an x-ray image recording system used with the invention and FIG. 2 shows a patient in the x-ray image recording system with a stent as the object on which the settings of the x-ray image recording system are based.

An x-ray image recording system shown in FIG. 1 and marked as a whole with 10, as known from DE 10 2005 012 700 A1, comprises a base frame 12, on which a carousel 14 is held in such a manner that it can rotate about a first axis of rotation. A rocker arm 16 is attached to the carousel 14 in such a manner that it can be pivoted about a second axis of rotation. An arm 18 is attached to the rocker arm 16 in such a manner that it can be rotated about a third axis of rotation. A hand 20 is attached to the end of the arm 18 in such a manner that it can be rotated about a fourth axis of rotation. The hand 20 has a securing element 22, which can be rotated about a rotational axis 23 and can be pivoted about a fifth axis of rotation perpendicular thereto.

A support, marked generally with the reference character 24, is coupled to the securing element 22 of the hand 20 (x-ray C-arm). The support is embodied in the manner of a U-profile (even a C-profile viewed from the side) with two opposing limbs 26, 26'. An x-ray detector 28 is attached to a first limb 26 and an x-ray radiation source 30 is attached to a second limb 26'.

The x-ray image recording system 10 comprises a controller 32 with a microprocessor 34. Linked to the controller 32 is a display unit 36 for displaying x-ray images. Data can be input by way of a computer mouse 38. A keyboard 40 is also provided, by way of which data can likewise be input.

Figure 2:
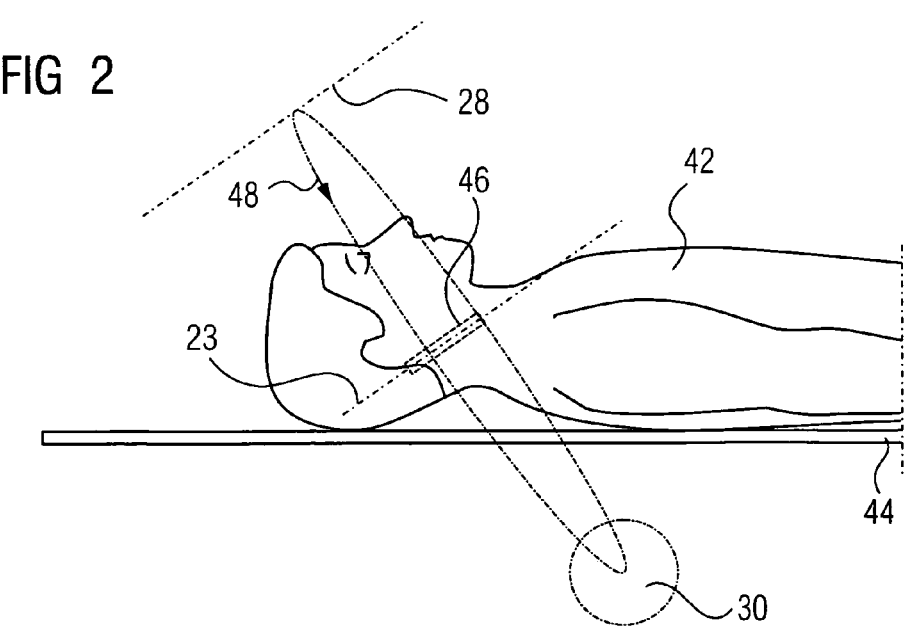

FIG. 2 shows a patient 42 on a patient table 44, which is disposed in the x-ray image recording system 10, so that the x-ray C-arm 24 can take up any positions in relation to the patient table 44.

It is now a matter of imaging a quite specific object. Such an object can be an anatomical region of the patient 42, for example a tumor, vessels or bones. The object can also be a medical apparatus introduced into the body of the patient 42, for example a biopsy needle, the tip of a catheter or a stent. FIG. 2 shows a stent 46 introduced into the body of the patient 42 as the object to be imaged. X-ray images of the patient 42 are now recorded in the region of the stent 46 in two positions of the x-ray C-arm. If the stent is not curved, it forms a straight tube, which is rotationally symmetrical. An axis can then be positioned uniquely through the stent 46, said axis being the axis of rotational symmetry of the stent 46. If the stent is curved, a specific axis can be defined in relation to each cross-section over different segments of the stent, with the axes gradually tilting toward each other. A center axis can then be selected as the marked axis at a center point of the stent 46.

It is now a matter of establishing such a marked axis in relation to the object, in the present instance the stent 46. To this end the x-ray image recording system 10 is used to record a first x-ray image and then to record a second x-ray image after rotating the x-ray C-arm 24, ideally through between 80 and 100 and preferably through 90 degrees. The stent 46 can be recognized in the x-ray images and a 2D axis line passing through the stent 46 can be plotted. This plotting operation can be carried out by a user, to whom the x-ray image is displayed on the display unit 36 of the x-ray image recording system 10, said user using the mouse 38 or in some instances the keyboard 40 to mark points in the x-ray image, which are used to define the axis. Alternatively a three-dimensional sample of the object, in the present instance therefore the stent 46, is stored in the processor 34 of the x-ray image recording system 10 (template) and an image recognition system running in the processor 34 is able to recognize structures produced by the stent 46 in the two 2D x-ray images, by comparing the gray-scale values in the x-ray images with the template. An axis defined in the template can then be plotted in the x-ray images.

If 2D axis lines are now plotted in the two x-ray images respectively, a 3D axis line can be determined by back-projection into a volume element space respectively. It is then possible to determine a center 3D axis line from the two 3D axis lines, if they do not correspond. To this end different points on the one 3D axis line are used respectively to determine the shortest distance to the other 3D axis line, a connecting line is calculated and a point, which is to be associated with the 3D axis line to be used ultimately, is defined on the half of the connecting line.

The result of the method is that a 3D axis line is defined in the volume element space, which reproduces an object axis of the object, in this instance the stent 46. The x-ray C-arm 24 is now moved so that the axis of rotation 23 corresponds to this axis line. This situation is shown in FIG. 2. A sequence of images can then be recorded, in which the x-ray C-arm is rotated simply by incorporating a single element 22 of the number of individual elements 12, 14, 16, 18, 20. The movement of the x-ray image recording system is not complicated by this but remains simple. When the x-ray C-arm is pivoted about the axis of rotation 23 according to the arrow 48, an x-ray image can be recorded in different positions respectively, so the stent 46 is considered from different sides. The prior precise definition of the object axis means that these views of the stent 46 in the x-ray images are such that the stent 46 is displayed optimally.

If the number of x-ray images in the sequence is sufficiently large, for example 200, a 3D reconstruction can be generated. This shows a better object resolution than when a more or less arbitrary axis is used when recording a sequence of images (in the present instance therefore of the stent 46 and also the tissue into which the stent 46 is introduced).

The method can be implemented in just the same manner for objects other than the stent 46. In the case of objects, to which object axes cannot be assigned so easily, for example an extended object like a tumor, it is possible to define an axis, which passes through the tumor for a distance of maximum length, so that the representation of the tumor in the x-ray images is ultimately as large as possible, when this axis is made to correspond to the axis of rotation 23.

The invention claimed is:

1. A method for activating an x-ray image recording system with an x-ray C-arm, comprising:
    positioning the x-ray C-arm to a first position;
    recording a first 2D x-ray image of a patient in the first position;
    positioning the x-ray C-arm to a second position;
    recording a second 2D x-ray image of the patient in the second position;
    defining a first 2D axis line in relation to an object of the patient in a first coordinate of the first 2D x-ray image;
    defining a second 2D axis line in relation to the object in a second coordinate of the second 2D x-ray image;
    back-projecting the first and the second 2D axis line into a volume element space;
    determining a 3D axis line in the volume element space from the back-projected first and second 2D axis line; and
    activating the x-ray image recording system by pivoting the x-ray C-arm about the 3D axis line.

2. The method as claimed in claim 1, wherein the first and the second 2D axis line is respectively defined based on a first set of two coordinate points and a second set of two coordinate points from an input of an operator or from an image recognition method.

3. The method as claimed in claim 2, wherein the two coordinate points of the first set are back-projected into the volume element space as a further 3D line.

4. The method as claimed in claim 3, wherein the 3D line and the further 3D line are forward-projected into the second coordinate system of the second 2D x-ray image and displayed to the operator in the second 2D x-ray image.

5. The method as claimed in claim 2, wherein a first and a second 2D coordinate point is respectively defined on the first and the second 2D axis line by a further input of the operator or by a calculation from the first and the second set of the two coordinate points or by the image recognition method.

6. The method as claimed in claim 5, wherein a 3D coordinate point is determined on the 3D axis line by back-projecting the first and the second 2D coordinate point in the volume element space.

7. The method as claimed in claim 6, wherein the x-ray image recording system is activated by corresponding the 3D coordinate point to a marked point defined between an x-ray radiation source and an x-ray detector of the x-ray C-arm.

8. The method as claimed in claim 7, wherein the marked point is an isopoint of the x-ray C-arm.

9. The method as claimed in claim 1, wherein a sensor is arranged on the object and is recognized in the first and the second 2D x-ray image.

10. The method as claimed in claim 9, wherein the sensor emits position and orientation data items and a coordinate system of the sensor is assigned to a coordinate system of the x-ray image recording system based on the first and the second 2D x-ray image.

11. The method as claimed in claim 10, wherein the first and the second 2D axis line is defined based on the data items emitted by the sensor.

12. The method as claimed in claim 1, wherein the x-ray image recording system is automatically activated.

13. An x-ray image recording system, comprising:
an x-ray C-arm with an x-ray radiation source and an x-ray detector that records a first 2D x-ray image of a patient in a first position and a second 2D x-ray image of the patient in a second position;
a computer that:
defines a first 2D axis line in relation to an object of the patient in a first coordinate of the first 2D x-ray image,
defines a second 2D axis line in relation to the object in a second coordinate of the second 2D x-ray image,
back-projects the first and the second 2D axis line into a volume element space,
determines a 3D axis line in the volume element space from the back-projected first and second 2D axis line, and
activates the x-ray image recording system by pivoting the x-ray C-arm about the 3D axis line.

14. The x-ray image recording system as claimed in claim 13, wherein the x-Ray C-arm is attached to a hand of a robot having six axes of rotation.

15. A method for activating an x-ray image recording system with an x-ray C-arm, comprising:
introducing a sensor into a body of a patient, the sensor emitting position and orientation data items in a coordinate system that is fixed and known in relation to a coordinate system of the x-ray image recording system;
receiving the data items in the x-ray image recording system;
determining a 3D axis line from the received data items; and
activating the x-ray image recording system by pivoting the x-ray C-arm about the 3D axis line.

16. The method as claimed in claim 15, wherein the x-ray image recording system is automatically activated.

* * * * *